United States Patent [19]
Weferling et al.

[11] Patent Number: 6,011,172
[45] Date of Patent: Jan. 4, 2000

[54] PROCESS FOR ALKYLATING ELEMENTAL PHOSPHORUS

[75] Inventors: Norbert Weferling, Hürth; Othmar Stelzer, Wuppertal; Günter Kolbe, Kerpen, all of Germany

[73] Assignee: Clariant GmbH, Frankfurt, Germany

[21] Appl. No.: 09/198,543

[22] Filed: Nov. 24, 1998

[30] Foreign Application Priority Data

Nov. 10, 1997 [DE] Germany ............................ 198 51 730
Nov. 28, 1997 [DE] Germany ............................ 197 52 736

[51] Int. Cl.$^7$ ...................................................... C07F 9/22
[52] U.S. Cl. ................................................................ 562/8
[58] Field of Search ...................................... 562/8

[56] References Cited

U.S. PATENT DOCUMENTS

| | | | |
|---|---|---|---|
| 3,579,576 | 5/1971 | Angstadt | 562/816 |
| 4,590,014 | 5/1986 | Wolf | 562/8 |
| 5,891,226 | 4/1999 | Kleiner | 106/18.18 |

OTHER PUBLICATIONS

"Superbase–Induced Generation of Phosphide and Phosphinite Ions as Applied in Organic Synthesis," B.A. Trofimov, N.K. Gusarova, S.F. Malysheva, T.N. Rakhmatulina and M.G. Voronkov, 1991, vol. 55, pp. 271–275.

"The Systems Elemental Phosphorus–Strong Bases as Synthetic Reagents," B. Trofimov, N. Gusarova, and L. Brandsma, Main Group Chem. News, 1996, vol. 4, No. 1, pp. 18–24.

"Generation of Phosphide Anions From Phosphorus Red and Phosphine in Strongly Basic Systems to Form Organylphosphines and –Oxides," B. Trofimov, N. Gusarova, L. Brandsma, Phosphorus, Sulfur and Silicon, 1996, vol. 109–110, pp. 601–604.

"Alkylation of Phosphine Ph$_3$ Generated from Red Phosphorus," D. Semenzin, G. Etemad–Moghadam, D. Albouy, and M. Koenig,; Tetrahedron Letters vol.35, No. 20, pp. 3297–3300, 1994.

CA:115:71753 abs of Phosphorus, Sulfur Silicon by Trofimov 55 (1–4) p.271, 1991.

CA:116:129058 abs of Z Anorg Allg Chem 606 pp.17–40 by Bock, 1991.

*Primary Examiner*—Gary Geist
*Assistant Examiner*—Jean F Vollano
*Attorney, Agent, or Firm*—Susan S. Jackson; Hesna J. Pfeiffer

[57] ABSTRACT

The invention relates to a process for preparing alkali metal salts and/or alkaline earth metal salts of alkylphosphonous acids and dialkylphosphinic acids from elemental yellow phosphorus and alkyl halides, which comprises carrying out the reaction in the presence of aqueous alkali metal hydroxide or alkaline earth metal hydroxide or mixtures thereof. The invention likewise relates to the use of the compounds prepared by the process according to the invention for preparing flame retardants, extraction media and plant protection agents.

13 Claims, No Drawings

PROCESS FOR ALKYLATING ELEMENTAL PHOSPHORUS

The invention relates to a process for preparing alkali metal salts and/or alkaline earth metal salts of alkylphosphonous acids and dialkylphosphinic acids from elemental yellow phosphorus and alkyl halides.

Organic phosphorus compounds are becoming of increasing industrial importance. They are principally used to prepare herbicides or as herbicides themselves, as extraction media and as flame retardants. The starting materials used are preferably $PH_3$ and phosphorus halides, which must in turn be prepared from yellow phosphorus.

To date, only a few processes are known by which organic phosphorus compounds having more than one phosphorus-carbon bond may be prepared from simple starting materials.

The reaction of red phosphorus in a superbasic medium dimethyl sulfoxide/potassium hydroxide (DMSO/KOH) with acetylenes or olefins as alkylating agents (Trofimov et al., Phosphorus, Sulfur and Silicon 55, 271, 1991) preferentially gives triorganylphosphines and triorganylphosphine oxides.

Alkylating red phosphorus with acrylonitrile predominantly leads, under the abovementioned conditions with ultrasonic treatment of the reaction mixture, to secondary phosphine oxide. If 1,1-diphenylethylene is used, this produces tertiary phosphine oxide (30%), secondary phosphine oxide (10%) and phosphinic acid (35%) [D. Semenzin et al., Tetrahedron letters 35, 3297, 1994].

An attempt has also been made (Trofimov et al., Main Group Chem. News 4, 18, 1996, Phosphorus, Sulfur and Silicon, 109/110, 601, 1996) to react elemental phosphorus, in its red modification, with alkyl halides in the presence of potassium hydroxide, water, dioxane and a phase-transfer catalyst. Tertiary phosphine oxides were found as main products (up to 75% with benzyl bromide, about 60–65% with butyl bromide). Secondary phosphine oxides and phosphinic esters were produced at 19% and 6%, respectively, as by-products, but the former only in the presence of zinc powder as reducing agent.

However, the abovementioned processes have the disadvantage that the red phosphorus or organophosphorus intermediates must be prepared first of all. These processes are highly complex industrially and thus are also not economical; the products produced must frequently be purified further, which is laborious. Just the specific preparation of certain compounds in a high yield is frequently particularly difficult.

Considerably more favorable, therefore, would be a synthesis which starts directly from elemental yellow phosphorus and which, using further, readily industrially available starting materials, would lead in a simple manner to the desired alkali metal salts or alkaline earth metal salts of alkylphosphinic acids and dialkylphosphinic acids.

The object therefore underlying the invention is to provide a process for preparing alkali metal salts and/or alkaline earth metal salts of alkylphosphinic acids and dialkylphosphinic acids which avoids the abovementioned disadvantages and by which the desired end products can be prepared without problem and in the appropriate mass ratios.

This object is achieved by a process of the type described at the outset, which comprises carrying out the reaction in the presence of aqueous alkali metal hydroxide or alkaline earth metal hydroxide or mixtures thereof.

Preferably, the reaction is carried out in a two-phase system of aqueous alkali metal hydroxide or alkaline earth metal hydroxide or mixtures thereof and an organic solvent.

Preferably, as alkyl halides, use is made of methyl chloride or methyl bromide.

Preferably, as organic solvents, use is made of unbranched or branched alkanes, alkyl-substituted aromatic solvents, water-immiscible, or only partially water-miscible, alcohols or ethers, alone or in combination with one another.

Particularly preferably, as organic solvent, use is made of toluene, alone or in combination with alcohols.

Preferably, the reaction is carried out in the presence of a phase-transfer catalyst.

Preferably, the phase-transfer catalyst is tetraalkylphosphonium halides, triphenylalkylphosphonium halides or tetraorganylammonium halides.

Preferably, the temperature in the reaction is from $-20$ to $+60°$ C.

Particularly preferably, the temperature is from 0 to $30°$ C.

Preferably, the reaction is carried out at a pressure of from 0 to 10 bar.

Preferably, the process according to the invention is carried out in such a manner that the yellow phosphorus is suspended in a solvent or a solvent mixture and then reacted with alkyl halide and a compound of the formula MOH or $M'(OH)_2$ or mixtures thereof, where M is an alkali metal and M' is an alkaline earth metal.

Preferably, the yellow phosphorus and the alkyl halide are reacted with one another in a molar ratio of from 1:1 to 1:3, the molar ratio of yellow phosphorus to the compound of the formula MOH or $M'(OH)_2$ being from 1:1 to 1:5.

Preferably, the two-phase system obtained after the reaction is separated and processed further as aqueous phase.

The invention also relates to the use of the alkali metal salts and/or alkaline earth metal salts of alkylphosphinic acids and dialkylphosphinic acids prepared according to the invention for preparing flame retardants, extraction media and plant protection agents.

Surprisingly, it has been found that elemental yellow phosphorus may be reacted by the process according to the invention with alkyl halides in the two-phase system (organic solvent/aqueous alkali metal hydroxide), and in the presence or absence of a (phase-transfer) catalyst, under extremely mild conditions to form a product mixture which comprises, as main product, the salt of the corresponding alkylphosphinic acid RP(:O)HOH. Further technically useful phosphorus-containing products found are salts of hypophosphorous and phosphorous acid, in addition to the equally valuable salt of dialkylphosphinic acid $R_2P(:O)OH$.

Small amounts of trialkylphosphine oxide $R_3P(:O)$, dialkylphosphine oxide and unidentified phosphorus compounds can also be formed in conjunction, which are removed from the product mixture in the usual way. In addition, as a by-product, hydrogen is formed, which can be separated off without problem from the reaction mixture.

Surprisingly, neither phosphine ($PH_3$), nor alkylphosphines ($RPH_2$, $R_2PH$), are formed in significant amounts by the process according to the invention. By choosing suitable reaction conditions, such as adding small amounts of alcohols to the organic phase, the formation of all unidentified phosphorus-containing by-products is minimized to a surprisingly small extent of a few mol % of the yellow phosphorus used, to the benefit of the three main products, namely the alkylphosphonite, hypophosphite and phosphite salts.

The process according to the invention can be carried out, for example, in such a manner that the solvent is introduced together with the phase-transfer catalyst and, if appropriate, heated above the melting point of the yellow phosphorus, then the elemental (yellow) phosphorus is added, the mixture is cooled with vigorous stirring to temperatures of, for example, from −10 to +30° C., and then the alkyl halide is added.

The reaction is started by adding alkali metal hydroxide solution. After completion of the reaction, the reaction system can be diluted, for example with water, and then the readily volatile components ($H_2$, $PH_3$, $RPH_2$, $R_2PH$ and excess alkyl halide) are removed.

By this means an aqueous/organic two-phase system is produced, whose phases are separated. The constituents from the phases are determined by analysis.

The aqueous phase can be worked up by the known processes of the prior art to produce the pure acids, such as alkylphosphinic acid, for example (by ion exchange or distillation, for instance).

In the abovementioned reaction, mixtures of alkali metal hydroxides and alkaline earth metal hydroxides can also advantageously be used, in order to separate off phosphite formed in the reaction, as $Ca(HPO_3)$ for example.

The reaction partners can also be added in a different sequence, for example by introducing these continuously in the abovedefined molar ratio into a reactor (pressurized tube, pressurized reactor or cascade) and discharging them again from the reactor after residence times of from 0.5 to 2 h. The organic phase obtained after the phase separation, which still comprises the majority of any phase-transfer catalyst used, is expediently recycled.

EXAMPLE 1

2 l of toluene and 25 g (0.05 mol) of tributylhexadecylphosphonium bromide were introduced into a 5-liter stainless steel pressurized reactor and heated to approximately 60° C. 62 g (2 mol) of molten yellow phosphorus were introduced into the reactor and then cooled with vigorous stirring to 0° C. 151 g (3 mol) of methyl chloride were then condensed in.

At 0° C., 600 g of a 56% strength KOH solution (6 mol KOH) were pumped in in the course of one hour. The heat of reaction was removed by cooling the reactor jacket and the temperature in the reactor interior during the addition time was kept to from 0 to +20C. After a post-reaction time of one hour at 0° C., the mixture was warmed to room temperature and the entire batch diluted with 1 l of water.

The reactor was expanded via a combustion system, the resulting hydrogen, excess methyl chloride and traces of gaseous phosphines ($PH_3$, $MePH_2$) being burnt. The residue obtained was two homogeneous liquid phases which no longer contained any yellow phosphorus. The phases were drained off separately and analyzed by $^{31}P$-NMR spectroscopy.

|  | aqueous phase (mol % phosphorus) |
|---|---|
| Trimethylphosphine oxide | 2.3 |
| Dimethylphosphinic acid potassium salt | 0.5 |
| Methyl phosponic acid potassium salt | 64.2 |
| Phosphorous acid potassium salt | 15.8 |
| Hypophosphorous acid potassium salt | 14.2 |
| Unidentified compounds | 3.1 |

EXAMPLE 2

The procedure of Example 1 was followed, but the reaction temperature was 25° C.

| Analysis: | aqueous phase (mol % phosphorus) |
|---|---|
| Trimethylphosphine oxide | 2.5 |
| Dimethylphosphinic acid potassium salt | 18.0 |
| Methylphosphinic acid potassium salt | 54.4 |
| Phosphorous acid potassium salt | 13.3 |
| Hypophosphorous acid potassium salt | 6.0 |
| Unidentified compounds | 5.7 |

EXAMPLE 3

500 ml of diethylene glycol diethyl ether, 13 g (0.026 mol) of tributylhexadecylphosphonium bromide and 93 g (1 mol) of n-butyl chloride were introduced into a 2 liter stirred flask. To this solution was added a solution of 150 g of NaOH (3.75 mol) in 150 g of water at room temperature.

15.5 g (0.5 mol) of molten yellow phosphorus were added dropwise in the course of 1 hour at 0° C. to the vigorously stirred two-phase mixture. After a further reaction time of 3 h, the two clear phases were separated and the resulting reaction products were characterized by $^{31}P$-NMR spectroscopy:

|  | aqueous phase (mol % phosphorus) |
|---|---|
| Butylphosphininc acid sodium salt | 41 |
| Hypophosphorous acid sodium salt | 3 |
| Phosphorous acid sodium salt | 56 |
| Unidentified compounds | <0.5 |

EXAMPLE 4

A solution of 26.1 [lacuna] (0.05 mol) of tributylhexadecylphosphonium bromide in 1000 ml of toluene was introduced into a 5 l stainless steel pressure reactor and preheated to 60° C. After addition of 62 g (2 mol) of yellow phosphorus, the mixture was cooled to −10° C. with intensive stirring and then 202 g (4 mol) of methyl chloride were condensed in. Thereafter, 400 g of 50% strength by weight aqueous sodium hydroxide solution were added in the course of 2 hours, the temperature being maintained at −10° C. 400 g of water were added in the course of one hour, the mixture was stirred thereafter for one further hour, heated to room temperature and then the reactor was depressurized via a combustion unit. This produced two homogeneous liquid phases which were separated and analyzed.

The aqueous phase (weight: 920 g) contained 65.6 mol % methylphosphinic acid, 14.9 mol % phosphorous acid and 13.7 mol % hypophosphorous acid and 2.8 mol % dimethylphosphinic acid in the form of sodium salts thereof.

EXAMPLE 5

A solution of 29 g (0.05 mol) of tetraoctylphosphonium bromide in 1000 ml of toluene was introduced into a 5 l stainless steel pressure reactor and preheated to 60° C. After addition of 62 g (2 mol) of yellow phosphorous, the mixture was cooled to −10° C. with intensive stirring and then 202 g (4 mol) of methyl chloride were condensed in. Thereafter, the mixture was heated to 20° C. and 400 g of 50% strength by weight aqueous sodium hydroxide solution were added in the course of 2 hours, the temperature being maintained at 20° C. 400 g of water were added in the course of one hour, thereafter the mixture was stirred for one further hour, heated to room temperature and then the reactor was depressurized via a combustion unit. This produced two homogeneous liquid phases which were separated and analyzed.

The aqueous phase (weight: 940 g) contained 51.2 mol % methylphosphinic acid, 24.7 mol % phosphorous acid and 18.5 mol % hypophosphorous acid and 2.6 mol % dimethylphosphinic acid in the form of sodium salts thereof.

The acids may be prepared in a known manner, for example by ion exchange, from the salts prepared in Examples 1 to 5.

We claim:

1. A process for preparing alkali metal salts and/or alkaline earth metal salts of alkylphosphinic acids and dialkylphosphinic acids from elemental yellow phosphorus and alkyl halides, which comprises carrying out the reaction in the presence of aqueous alkali metal hydroxide or alkaline earth metal hydroxide or mixtures thereof.

2. The process as claimed in claim 1, wherein the reaction is carried out in a two-phase system of aqueous alkali metal hydroxide or alkaline earth metal hydroxide or mixtures thereof and an organic solvent.

3. The process as claimed in claim 1, wherein the alkyl halides, are methyl chloride or methyl bromide.

4. The process as claimed in claim 1, wherein the organic solvent is chosen from the group consisting of unbranched or branched alkanes, alkyl-substituted aromatic solvents, water-immiscible, or only partially water-miscible, alcohols or ethers, alone or in combination with one another.

5. The process as claimed in claim 1, wherein the organic solvent is toluene, alone or in combination with alcohols.

6. The process as claimed in claim 1, wherein the reaction is carried out in the presence of a phase-transfer catalyst.

7. The process as claimed in claim 6, wherein the phase-transfer catalyst is tetraalkylphosphonium halides, triphenylalkylphosphonium halides or tetraorganylammonium halides.

8. The process as claimed in claim 1, wherein the temperature in the reaction is from −20 to +60° C.

9. The process as claimed in claim 1, the temperature is from 0 to 30° C.

10. The process as claimed in claim 1, wherein the reaction is carried out at a pressure of from 0 to 10 bar.

11. The process as claimed in claim 1, wherein the yellow phosphorus is suspended in a solvent or a solvent mixture and then reacted with an alkyl halide and a compound of the formula MOH, or M' $(OH)_2$ or mixtures thereof, where M is an alkali metal and M' is an alkaline earth metal.

12. The process as claimed in claim 1, wherein the yellow phosphorus and the alkyl halide are reacted with one another in a molar ratio of from 1:1 to 1:3, the molar ratio of yellow phosphorus to the compound of the formula MOH or M' $(OH)_2$ being from 1:1 to 1:5.

13. The process as claimed in claim 1, wherein the two-phase system obtained after the reaction is separated and processed further.

* * * * *